(12) United States Patent
Götz

(10) Patent No.: US 8,030,949 B2
(45) Date of Patent: Oct. 4, 2011

(54) MEASUREMENT METHOD FOR DETERMINING MOISTURE CONTENT

(75) Inventor: Meinrad Götz, Bonndorf (DE)

(73) Assignee: Testo AG, Lenzkirch (DE)

( * ) Notice: Subject to any disclaimer, the term of this patent is extended or adjusted under 35 U.S.C. 154(b) by 419 days.

(21) Appl. No.: 12/263,036

(22) Filed: Oct. 31, 2008

(65) Prior Publication Data

US 2010/0109635 A1    May 6, 2010

(51) Int. Cl.
*G01R 27/26*    (2006.01)
(52) U.S. Cl. .......................... 324/664; 324/686; 324/689
(58) Field of Classification Search .................. 324/664, 324/663, 658, 649, 600, 689, 686, 634
See application file for complete search history.

(56) References Cited

U.S. PATENT DOCUMENTS

| | | | | |
|---|---|---|---|---|
| 4,607,238 A | * | 8/1986 | Kohsiek | 331/143 |
| 4,662,220 A | * | 5/1987 | Laue | 73/335.02 |
| 5,014,908 A | * | 5/1991 | Cox | 236/44 E |
| 5,861,755 A | * | 1/1999 | Moerk et al. | 324/663 |
| 7,084,644 B2 | * | 8/2006 | Haider | 324/664 |
| 7,605,710 B2 | * | 10/2009 | Crnkovich et al. | 340/604 |

FOREIGN PATENT DOCUMENTS

GB    2242279 A    *   9/1991

OTHER PUBLICATIONS

Sensirion / The Sensor Company: "SHT1x / SHT7x Humidity & Temperature Sensor", Chapter 3, v2.02, Jul. 2004, pp. 1-9.

* cited by examiner

*Primary Examiner* — Hoai-An D Nguyen
(74) *Attorney, Agent, or Firm* — Hoffmann & Baron, LLP

(57) ABSTRACT

In a method for capacitive determination of the moisture content in a gas to be measured, it is provided that a capacitive element (2) brought into contact with a gas to be measured is operated in the manner of an RC oscillator (5) in charge-discharge cycles (27, 28), with the moisture content of the gas to be measured being determined from the time duration of a cycle. To assess measurement errors brought about by contaminants or aging effects, a measure for the time duration of a charging process (27) and a discharging process (28) is determined from output signal (26) of RC oscillator (5) and is processed with the measurement signal for the moisture content into a corrected measurement signal.

18 Claims, 4 Drawing Sheets

MEASUREMENT METHOD FOR DETERMINING MOISTURE CONTENT

Figure 1:
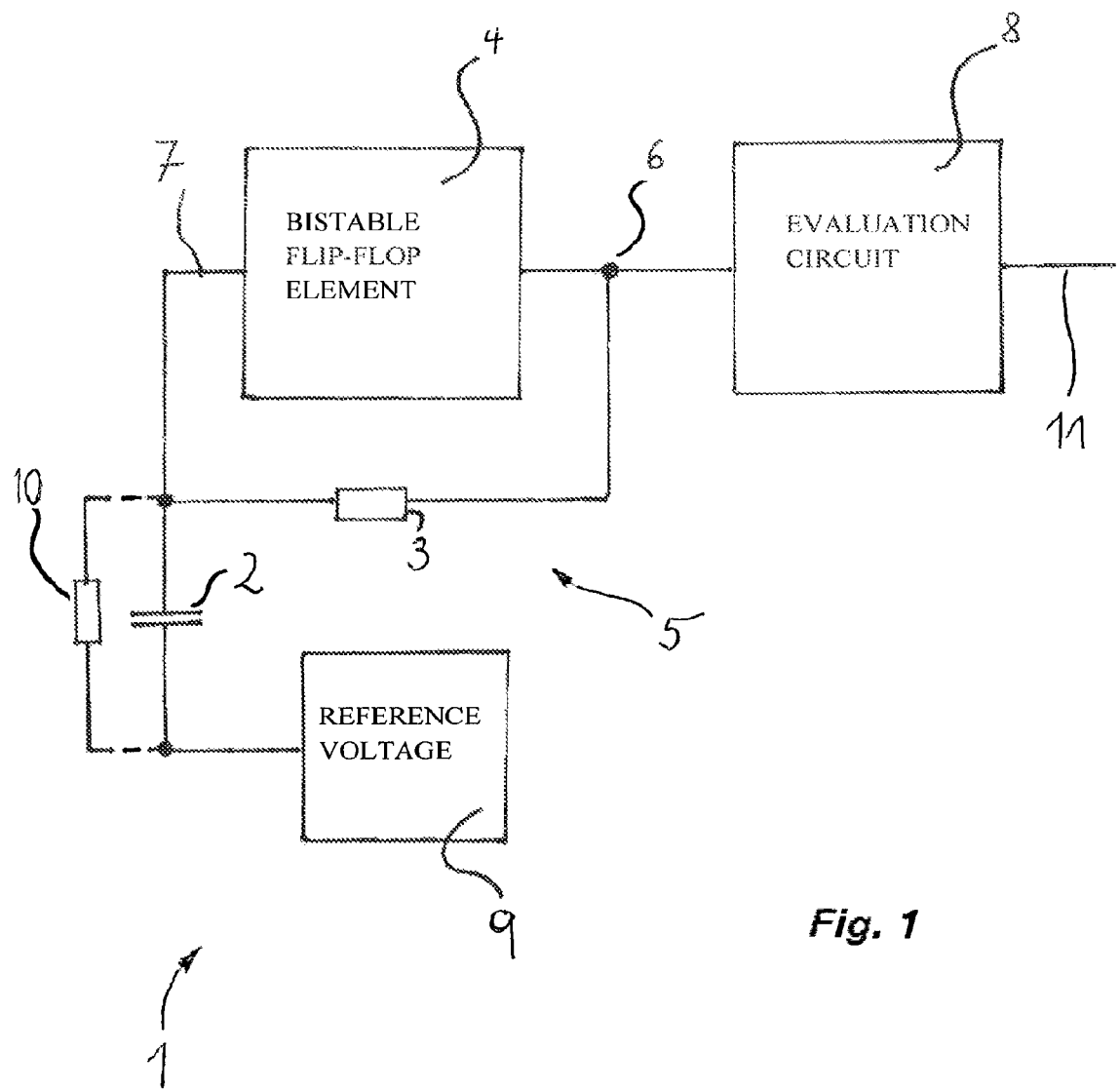

The invention relates to a measurement method for determining the moisture content in a gas to be measured, wherein a capacitive element constructed as a measurement sensor forms part of an RC oscillator that operates the capacitive element in charge-discharge cycles, wherein the capacitance of the capacitive element is moisture-dependent, and the capacitance-dependent oscillation frequency of the output signal of the RC oscillator is determined as the measurement signal.

The invention further relates to a measurement sensor for determining the moisture content in a gas to be measured, wherein the measurement sensor has a capacitive element, the capacitance of which is dependent on the moisture content of the gas to be measured, wherein the capacitive element is electronically supplemented to form an RC oscillator, and the RC oscillator generates a periodic output signal composed of semi-oscillations, the oscillation frequency of which signal is variable with the capacitance of the capacitive element, one semi-oscillation being associated with a charging process and another semi-oscillation with a discharging process of the capacitive element.

The measurement of the moisture content in gases, and in the air in particular, by means of capacitive sensors is frequently performed by a measurement circuit based on an oscillator circuit, in which a frequency dependent on the moisture is generated and evaluated by means of a moisture sensor constituted by a capacitor and either an inductor or a resistor. The problematic aspect in circuits operating on the basis of an RC oscillator is that, in addition to the capacitance change of the moisture sensor, changes in resistance, in particular, parasitic resistances on the moisture sensor, influence the measurement frequency. Such changes in resistance arise, among other things, because assembly components attract moisture and thus change their resistance, or a small conductive layer can form on the surface of assembly parts due to contamination and/or condensation. The quality of the moisture sensor also changes with moisture and temperature so that, in addition to the change in capacitance due to the moisture, resistance changes also result, which can likewise have an effect on the measurement frequency, and thus a cross-sensitivity arises that cannot be compensated.

If one views the moisture sensor as an actual capacitor, then a precise assessment of the sensor is possible only if one determines both the capacitance and the ohmic component of the sensor. This is not possible with the oscillator circuits previously used, since they supply a variable frequency that is determined both by the capacitance and by the loss resistance.

The invention is based on the problem of creating a method and a device for determining the moisture in gases with which an assessment of a moisture sensor in use is possible.

To solve this problem, it is provided in a method of the type mentioned above that information on the time duration of the charging section and/or information on the time duration of the discharge section is obtained within a charge-discharge cycle by means of an evaluation circuit and that correction information for the evaluation of the measurement signal is determined from the information obtained. The invention thus makes use of the recognition that the output signal of the RC oscillator, ideally symmetrical with respect to the time durations of the charge and discharge sections, is deformed by parasitic resistances that appear due to the above-described moisture influences, so that a statement on the sensor status and thus a precise assessment of the sensor is possible by means of a comparison of the time durations of the sections. This comparison of the time durations of the sections can be performed by determining the time duration of a section and a comparison to the time duration of a complete cycle or by comparison of the time durations of the sections to one another by means, for instance, of quotient formation or difference formation, or can be performed in another manner.

In one configuration of the invention it can be provided that the information on the time duration of the charge section and/or the discharge section is the respective time duration, preferably determined by a real-time clock or a timer. For instance, it can be provided for this purpose that the output signal of the RC oscillator is digitally detected and evaluated by software.

According to one advantageous configuration, it can be provided that the information on the time duration of the charge section is the voltage across an additional capacitor charged with a constant voltage during the charge section and/or the information on the time duration of the discharge section is the voltage across the additional capacitor charged or discharged during the discharge section with a voltage opposite to and with the same magnitude as the constant voltage. Thus a simple means for obtaining information on the time durations is described, in which the time duration is determined by the amount of charge accumulated on the capacitor, or drained out of the capacitor, during the sections. It is advantageous in this regard that a signal containing the unambiguous information on the time duration of the respective section and suitable for the subsequent further processing is generated with the generated voltage on the capacitor.

It is particularly advantageous if the constant voltage is the amplitude of the voltage signal that is generated by the RC oscillator and whose frequency is used to determine the moisture content. Thereby, additional means for determining the time, such as a real-time clock or timer, can be forgone, whereby the equipment construction is simplified overall.

According to one configuration of the invention, it can be provided that the correction actor is determined from the information obtained, which after several cycles or over several cycles settles into an equilibrium and/or into a mean value over time. Since the successive charging and discharging processes do not lead to a respective fully charged or fully discharged capacitor, an equilibrium value for the voltage at the capacitor arises after several cycles, about which the voltage at the capacitor fluctuates in the course of the cycle. The average of this voltage over time is dependent on the time duration of the charge section and the discharge section. Thus a simple means is described with which an electronic output signal can be generated that allows a direct conclusion to be drawn regarding the ratio of the time duration of the two sections of a cycle, with the possibility of forgoing the use of components for the numerical post-processing of measurement data such as the formation of quotients or differences.

For a simple assessment of the sensor status, it can be provided that the quotient from the numerical values of the information items obtained is calculated in order to determine the correction information.

To generate a signal suitable for further electronic processing it can be provided that the output signal of the RC oscillator is converted via an RC filter into a smoothed signal, preferably a DC signal, the mean voltage level of which is used to determine the correction value. It is advantageous that, after having reached an equilibrium state, the charging and discharging processes running in the RC filter, driven by the output signal of the RC oscillator, generate a DC voltage signal that allows an inference for an assessment of the sensor.

To monitor the sensor quality and/or the reliability of the measurement method, it can be provided that information and/or a signal is output whenever the correction value departs from a predetermined permissible value range. Thereby the necessity of a sensor exchange can be indicated, for example.

To solve the above-mentioned problem in a measurement sensor of the type mentioned above, it is provided that an evaluation circuit, with which the time durations and/or the ratio of the time durations of the semi-oscillations of the output signal can be determined, is connected to the output of the RC oscillator. Semi-oscillations of the output signal refer in this regard to the two sections of a cycle in the output signal that are separated by a zero-crossing point. The evaluation circuit thus allows, as already described with respect to the method according to the invention, a precise assessment of the sensor based on the deformation of the output signal over time.

To determine the time durations, a timer or some other means for time measurement can be provided for the assessment circuit, for example.

In an additional embodiment it can be provided that the assessment circuit has an additional capacitor that can be charged or discharged from the output signal of the RC oscillator via a resistor, and that the voltage dropping across the additional capacitor can be detected in the equilibrium state and/or in the average over time with the assessment circuit. Thus means are described with which time durations of sections are achievable indirectly via measurement of the accumulated or drained charge quantities.

A particularly favorable design results if the RC oscillator for generating the periodic output signal has a bistable flip-flop element. It is advantageous in this regard that additional timers can be forgone.

In one configuration of the invention it can be provided that the bistable flip-flop element has one input and one output, and that the voltage level at the output, preferably its sign, can be determined by a voltage present at the input. The voltage present at the input is preferably defined or determined by the voltage present at the capacitive element of the measurement sensor. The bistable flip-flop element preferably has a hysteresis behavior, whereby an output signal having steep flanks and a persistent signal level can be generated at the RC oscillator.

To generate an output signal that is suitable for the further processing and assessment of the measurement sensor, it can be provided that the capacitive element of the measurement sensor is arranged between the input of the bistable flip-flop element and a constant-voltage source.

To utilize the bistable flip-flop for the generation of the periodic output signal at the RC oscillator, it can be provided that the output of the bistable flip-flop element is connected to its input and the capacitive element, preferably via a resistor.

The invention will now be described on the basis of an embodiment, but is not limited to this embodiment. Additional embodiments arise by combination of the characteristics of the described embodiment with one another and/or with characteristics of the claims.

The following are shown:

FIG. 1, a circuit for determining the moisture in gases by means of a capacitive sensor in a representation of its principle.

Figure 2:
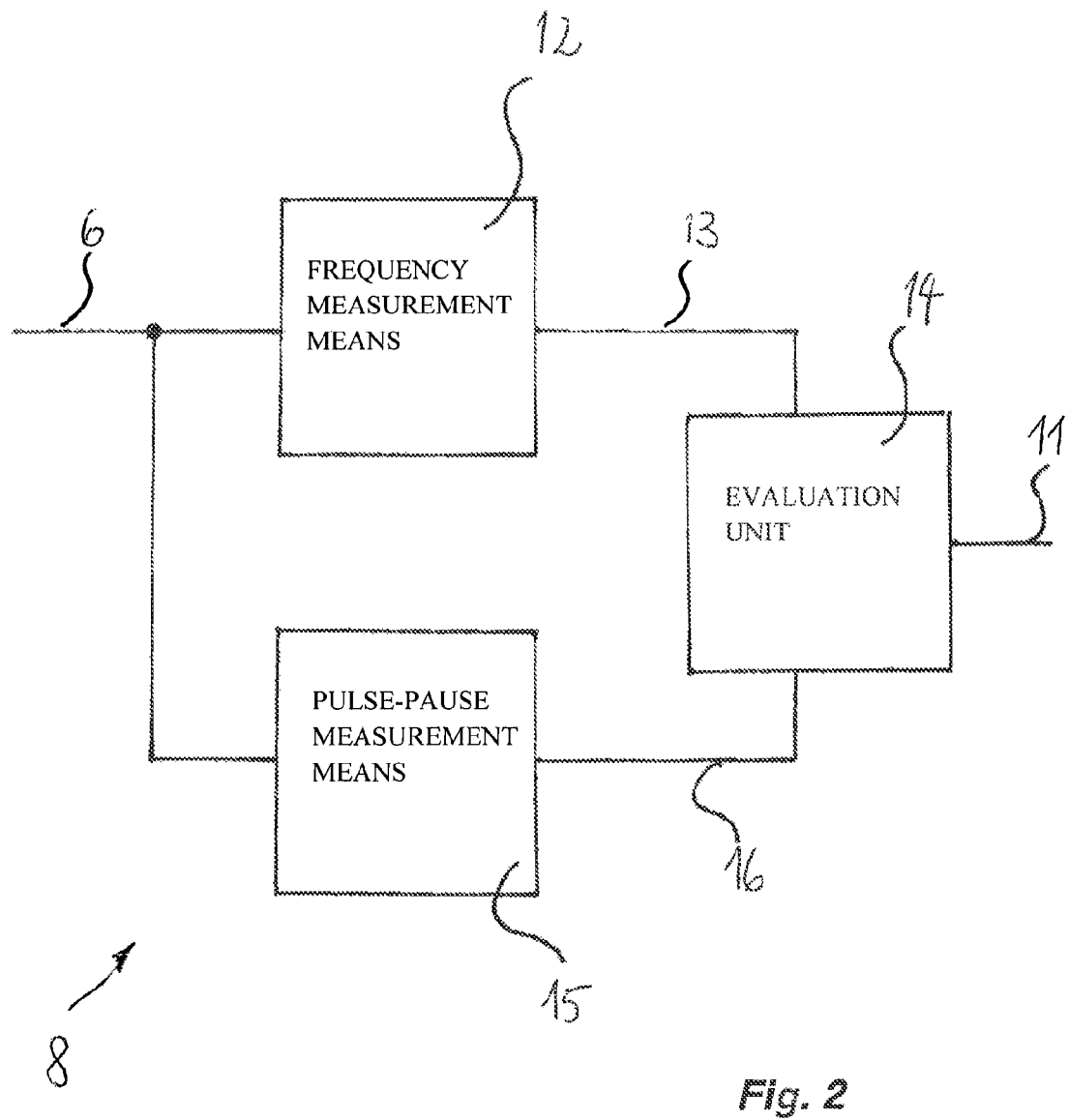

FIG. 2, a detail representation of the evaluation circuit from FIG. 1.

Figure 3:
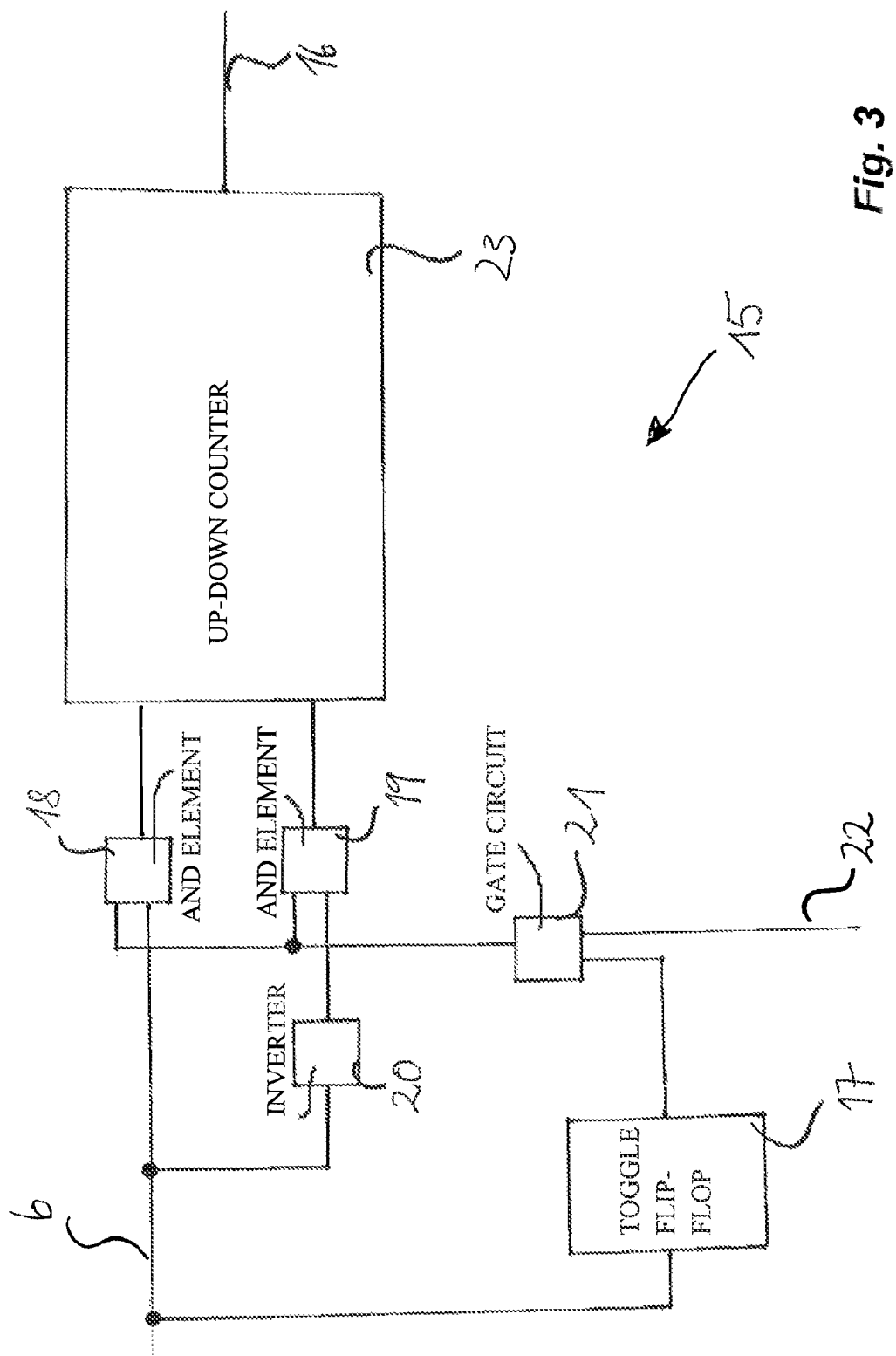
Figure 4:
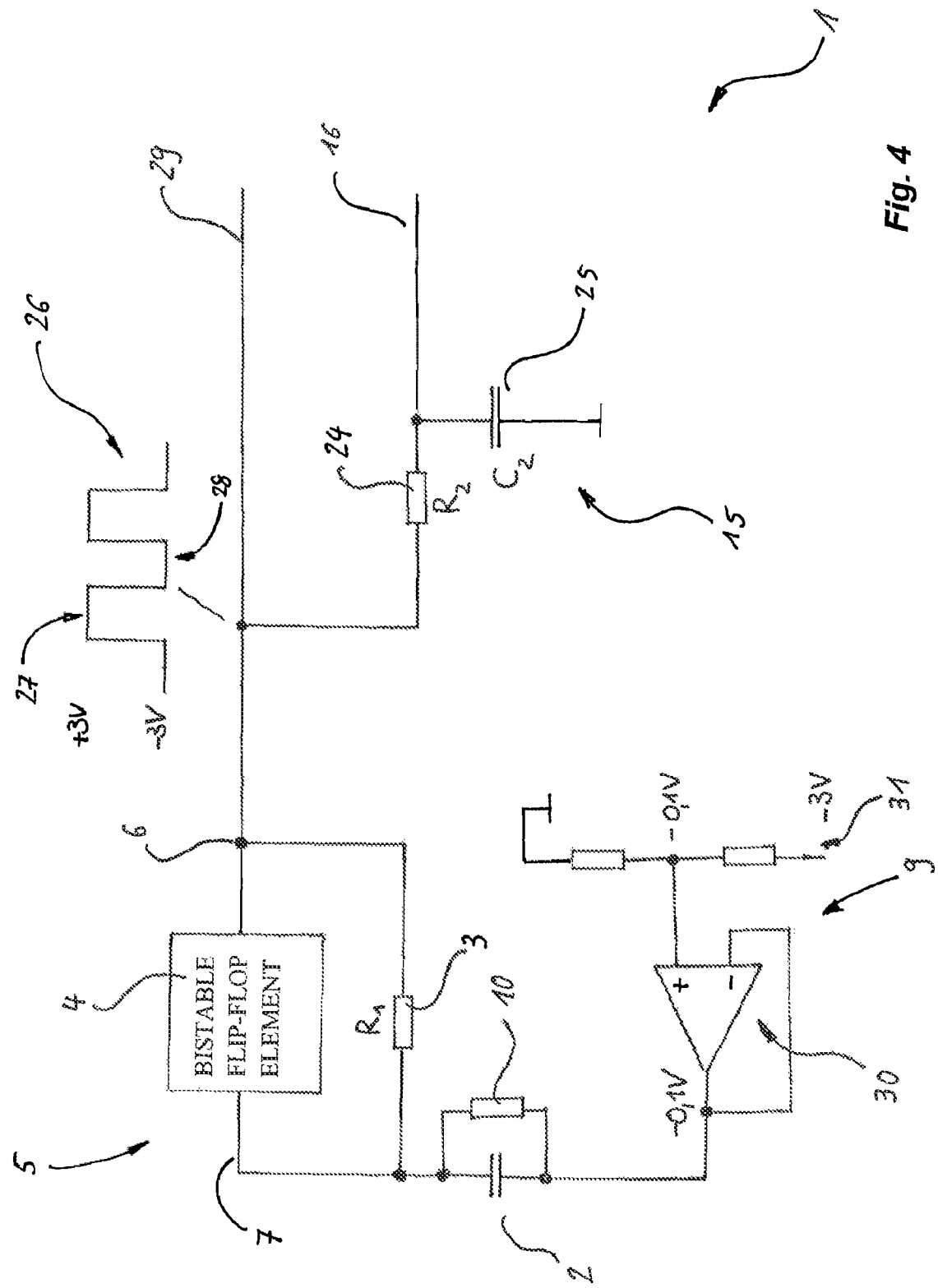

FIG. 3, a schematic representation of the pulse-pause measurement from FIG. 2, and FIG. 4, another embodiment of the invention, with a means for pulse-pause measurement that can do without a reference clock pulse and digital counting means.

A measurement sensor labeled 1 as a whole has a capacitive element 2, the capacitance of which is dependent on the moisture content of a gas to be measured put in contact with capacitive element 2.

Capacitive element 2 is supplemented by an ohmic resistor 3 and a bistable flip-flop element 4, a toggle flip-flop, to form an RC oscillator 5.

The bistable flip-flop element thus generates a voltage at its output 6 that causes a charging or discharging of capacitive element 2 via resistor 3, whereby the voltage at input 7 of bistable flip-flop element 4 changes. In case of a change in the input voltage above a threshold value, flip-flop element 4 jumps to a different state and generates a voltage of opposite polarity at output 6.

Thus, RC oscillator 5 operates capacitive element 2 in successive charge-discharge cycles. Since the period of these cycles is dependent on the capacitance of capacitive element 2 and this capacitance is moisture-dependent, the oscillation frequency of output signal 6 of RC oscillator 5 can be used to determine the moisture content at capacitive element 2.

The periodic output signal generated by RC oscillator 5 is thus composed of semi-oscillations, one semi-oscillation being associated with a respective charging process and the semi-oscillation following this semi-oscillation being associated with a respective discharging process of capacitive element 2.

An evaluation circuit 8, with which time durations, in particular, the ratio of the time durations of the semi-oscillation of output signal 6, can be determined, is connected to output 6 of RC oscillator 5.

For charging or discharging capacitive element 2 during the semi-oscillations, i.e., the charging and discharging sections, of the periodic output signal generated by RC oscillator 5, capacitive element 2 is connected at its other terminal to a stabilized reference voltage 9. This reference voltage forms the mean value for the voltage of the output signal at output 6 and can also be 0 V.

Moisture and surface effects at capacitive element 2 cause a parasitic resistance 10 to be present, which shortens the discharge of capacitive element 2 and lengthens the charging of capacitive element 2.

With this change of the time durations of the charging section and the discharging section, an assessment of measurement sensor 1 at evaluation circuit 8 is feasible, since information on the time duration of the charging section and the time duration of the discharging section is exactly what can be obtained with this evaluation circuit 8.

From the above information, evaluation circuit 8 provides correction information at its output 11 for evaluating the measurement signal of measurement sensor 1.

Measurement sensor 1 for determining the moisture content of the gas to be measured that is in contact with capacitive element 2 is evaluated in a known manner by evaluating the frequency of the output signal present at output 6.

FIG. 2 shows a representation of the principle of an evaluation circuit 8 from FIG. 1.

Evaluation circuit 8 has means 12 for frequency measurement, with which the frequency or period duration of the periodic output signal present at output 6 of RC oscillator 5 can be determined.

The means 12 for frequency measurement supplies a voltage signal at its output 13 that is dependent on the frequency of the output signal at output 6 of RC oscillator 5.

Since the charge or discharge time of capacitive element 2 without the parasitic resistance 10 is expressed by the formula:

$$t_{charge,ideal} = R \cdot C \cdot \ln 2 = t_{discharge,ideal}$$

it is thus possible, via the time duration of a charge-discharge cycle or the frequency of the output signal of RC oscillator 5, to determine the capacitance of capacitive element 2, and by means of a measurement table, the moisture content of the gas to be measured.

The result of the frequency measurement present at output 13 is supplied to an evaluation unit 14.

The information necessary to assess the sensor state via the time duration of the charge section or the discharge section is provided by a means 15 for pulse-pause measurement that is connected to output 6 of RC oscillator 5.

The means 15 for pulse-pause measurement is formed to determine the time durations of the semi-oscillations of the output signal present at output 6, and generates at its output 16 a result signal, which is likewise supplied to assessment unit 14.

From the result signals for frequency measurement and pulse-pause measurement supplied to it, assessment unit 14 generates a corrected moisture content signal that is output at output 11 of evaluation circuit 8.

FIG. 3 shows a block schematic diagram illustrating the construction principle of a means for pulse-pause measurement 15 from FIG. 2.

The output signal present at output 6 of RC oscillator 5 is supplied to a toggle flip-flop 17 and two AND elements 18 and 19, the signal for AND element 19 being conveyed via an inverter 20.

Via toggle flip-flop 17, a signal that enables a gate circuit 21 for one period of the output signal is obtained from the output signal.

A reference clock pulse 22 for exactly one period of the output signal present at output 6 reaches the second inputs of AND elements 18, 19 via this gate circuit 21.

For the duration of the charging process in RC oscillator 5, reference clock pulse 22 reaches, via AND element 18, an up-down counter 23, which can be realized both by digital components and by a microcontroller.

Up-down counter 23 is constructed such that it counts up as long as pulses reach up-down counter 23 via AND component 18.

Because of inverter 20, reference clock pulse 22 reaches up-down counter 23 via AND component 19 for the duration of the discharging process in RC oscillator 5. Up-down counter 23 now counts backwards as long as pulses reach it via AND component 19.

Thus, the numerical value formed in the charging process in up-down counter 23 is a measure of the charging time of capacitive element 2, and the numerical value formed during the discharging process is a measure of the difference between charge and discharge times, and thus a measure for the deviations of measurement sensor 1 from the ideal behavior.

Up-down counter 23 sends a signal corresponding to this measurement to output 16 of the means 15 for pulse-pause measurement.

FIG. 4 shows another embodiment, with a means 15 for pulse-pause measurement that can do without a reference clock pulse and digital counting means.

In the embodiment according to FIG. 4, identical numbers signify components identical to those in the embodiment according to FIGS. 1-3.

The means 15 for pulse-pause measurement in FIG. 4 has a resistor 24 and a capacitor 25 that are coupled in the manner of a lowpass filter to output 6 of RC oscillator 5.

The output signal 26 present at output 6, which signal has different voltage levels in charging sections 27 and discharging section 28, causes a charging or discharging of capacitor 25 via resistor 24.

Due to this succession of charging and discharging processes at capacitor 25, a signal arises at output 16 of means 15 for pulse-pause measurement in DC status that is smoothed with respect to output signal 26 and whose voltage level depends on the time durations of the semi-oscillations of output signal 26, i.e., of the signal during the charging sections 27 and discharging sections 28. This voltage level, interpreted as a DC voltage signal, can be further used for assessing measurement sensor 1 and is supplied to an evaluation unit 14 analogously to the circuit of FIG. 2.

Output signal 26 for frequency measurement and thus for determining an uncorrected moisture content is supplied, analogously to FIG. 2, at an output 29 to a means 12 for frequency measurement.

The basis of the circuits according to FIGS. 1-4 is thus an RC oscillator 5, in which a capacitive element 27 of a moisture sensor is charged and discharged via a resistor 3. The reference point of capacitive element 2 is connected to a reference voltage 9, by means, for instance, of the connection shown in FIG. 4 of a fed-back operational amplifier 30 to a voltage divider 31 that is set to a small reference voltage near zero.

If capacitive element 2 has no ohmic loss resistance 10, then one obtains the square-wave signal 26 shown in FIG. 4, whose pulse-pause ratio is 1:1.

If a loss resistance is formed in capacitive element 2, or the quality of the measurement sensor changes overall, then this has the effect of a loss resistance 10 inserted in parallel to capacitive element 2. In the charging phase 27, current must additionally be driven through loss resistance 10, which results in a longer charging time. In discharging phase 28 the capacitive element additionally discharges via loss resistance 10, which leads to a shorter discharge time. The result is a pulse-pause ratio that is no longer 1:1. This modified pulse-pause ratio is evaluated, as explained in detail in FIGS. 2-4, and a correction value for the actual measurement frequency is obtained therefrom.

In additional embodiments, the pulse-pause behavior is either determined by a precise time measurement in a digital manner, preferably with a microcontroller, or output signal 26 is converted by means of an RC filter into a DC voltage at output 16 that is proportional to the pulse-pause ratio, or at least unambiguously determined thereby. The DC voltage obtained by the RC filter is converted by means of an A/D converter into a suitable digital value for the microcontroller, so that the actual measurement signal can be corrected mathematically there.

Taking into account the loss resistance $R_v$ in FIG. 4, the pulse-pause ratio results according to the following formula:

$$\frac{t_{charge}}{t_{discharge}} = \frac{(R + R_v) \cdot C \cdot \ln 2}{(R - R_v) \cdot C \cdot \ln 2}$$

Thus a loss resistance $R_v$, having its origin in the loss resistance of capacitive element 2 and measurement sensor 1 as whole, can be derived from the charge and discharge time:

$$R_v = R \frac{(t_{charge} - t_{discharge})}{(t_{charge} + t_{discharge})}$$

The pulse-pause ratio can be evaluated in additional embodiments by an RC filter that forms the arithmetic mean of the square-wave voltage forming output signal 26. The obtained voltage is proportional to the pulse-pause ratio of the measurement frequency, or is at least unambiguously determined by it, and can be acquired by means of an analog/digital converter and supplied to a microcontroller for further processing.

In the method for capacitive determination of the moisture content in a gas to be measured, it is provided that a capacitive element 2 brought into contact with the gas to be measured is operated in the manner of an RC oscillator 5 in charge-discharge cycles 27, 28, with the moisture content of the gas to be measured being determined from the time duration of a cycle. To assess the measurement error caused by contaminants or aging effects, a measure for the time duration of a charging process 27 and a discharging process 28 is determined from output signal 26 of RC oscillator 5, and is processed with the measurement signal for the moisture content into a corrected measurement signal.

The invention claimed is:

1. Method for determining the moisture content in a gas to be measured, wherein a capacitive element (2) constructed as a measurement sensor (1) forms a part of an RC oscillator (5) that operates the capacitive element in charge-discharge cycles, wherein the capacitance ($C_1$) of capacitive element (2) is moisture-dependent and the capacitance-dependent oscillation frequency of output signal (26) of RC oscillator (5) is determined as the measurement signal, said method comprising: obtaining, within a charge-discharge cycle of the capacitive element, information on the time duration of the charging section (27) and information on the time duration of the discharging section (28) by means of an evaluation circuit (8), comparing the obtained information with an ideal pulse-pause ratio of the capacitive element based on the capacitive element operating with no moisture-dependent parasitic resistance, determining correction information for the assessment of the measurement signal from the step of comparing the obtained information with the ideal pulse-pause ratio, and adjusting the measurement signal by the correction information to obtain the moisture content in the gas to be measured.

2. Method according to claim 1, wherein the information on the time duration of charging section (27) and the information on the time duration of discharging section (28) is the respective time duration determined with a real-time clock or a timer (22).

3. Method according to claim 1, wherein the information on the time duration of charging section (27) is the voltage across an additional capacitor (25, $C_2$) charged with a constant voltage during charging section (27) and the information on the time duration of discharging section (28) is the voltage across the additional capacitor (25, $C_2$) charged or discharged with a voltage of opposite sign and equal magnitude as the constant voltage during discharging section (28).

4. Method according to claim 3, wherein the constant voltage is the amplitude of the output signal (26) that is generated by RC oscillator (5) and whose frequency is used for determining moisture content.

5. Method according to claim 1, wherein a correction factor is determined from the correction information obtained that arises after several cycles or over several cycles in equilibrium and/or in an average over time.

6. Method according to claim 1, wherein the step of determining correction information includes determining a quotient and/or a difference between the obtained information and the ideal pulse-pause ratio.

7. Method according to claim 1, wherein the output signal of RC oscillator (5) is converted via an RC filter (15, 24, 25) into a smoothed signal, the mean voltage level of which is used to determine the correction information.

8. Method according to claim 6, wherein the correction information is output whenever the quotient or the difference leaves a predetermined permissible value range.

9. Method according to claim 7, wherein the smoothed signal is a DC voltage signal.

10. Measurement sensor for determining the moisture content of a gas to be measured, said measurement sensor (1) comprising: a capacitive element (2), the capacitance of which is dependent on the moisture content of the gas to be measured, wherein the capacitive element (2) is electronically complemented to form an RC oscillator and the RC oscillator (5) generates from combined semi-oscillations a periodic output signal (26) whose oscillation frequency is variable with the capacitance ($C_1$) of the capacitive element (2); means for pulse-pause measurement for measuring the duration of a semi-oscillation associated with a charging process (27) of the capacitive element and of a semi-oscillation associated with a discharging process (28) of the capacitive element (2); and, an evaluation circuit (8), with which the time durations and/or the ratio of the time durations of the semi-oscillations (27, 28) of the output signal (26) can be determined, is connected to output (6) of the RC oscillator (5).

11. Measurement sensor according to claim 10, wherein the evaluation circuit (8) has a timer (22) and/or a means (23) for measuring time.

12. Measurement sensor according to claim 10, wherein the evaluation circuit (8) has an additional capacitor (25) that can be charged or discharged from the output signal (26) of the RC oscillator (5) via a resistor (24), and in that the voltage dropping across the additional capacitor (25, $C_2$) can be detected in the equilibrium state and/or in an average over time with the evaluation circuit (8).

13. Measurement sensor according to claim 10, wherein the RC oscillator (5) has a bistable flip-flop element (4).

14. Measurement sensor according to claim 13, wherein the bistable flip-flop element (4) has an input (7) and an output (6), and in that the voltage level present at output (6) can be determined by a voltage present at input (7).

15. Measurement sensor according to claim 13, wherein the bistable flip-flop element (4) has a hysteresis behavior.

16. Measurement sensor according to claim 13, wherein the capacitive element (2) of the measurement sensor (1) is arranged between input (7) of the bistable flip-flop element (4) and a constant voltage source (9).

17. Measurement sensor according to claim 13, wherein the bistable flip-flop element (4) has an input (7) and an output (6), the output (6) of the bistable flip-flop element (4) being connected to the input (7) and the capacitive element (2).

18. Measurement sensor according to claim 17, wherein the output (6) of the bistable flip-flop element (4) is connected to the input (7) and the capacitive element (2) via a resistor (3).

* * * * *

UNITED STATES PATENT AND TRADEMARK OFFICE
CERTIFICATE OF CORRECTION

Page 1 of 1

PATENT NO. : 8,030,949 B2
APPLICATION NO. : 12/263036
DATED : October 4, 2011
INVENTOR(S) : Meinrad Götz It is certified that error appears in the above-identified patent and that said Letters Patent is hereby corrected as shown below:

Column 2, line 37, replace "provided that the correction actor is determined from the" with --provided that the correction factor is determined from the--.

Signed and Sealed this
Twentieth Day of December, 2011

David J. Kappos
*Director of the United States Patent and Trademark Office*